(12) United States Patent
Sano et al.

(10) Patent No.: US 10,987,493 B2
(45) Date of Patent: Apr. 27, 2021

(54) GUIDE WIRE

(71) Applicant: NIPRO CORPORATION, Osaka (JP)

(72) Inventors: Yoshihiko Sano, Osaka (JP); Katsuhiro Hiejima, Osaka (JP)

(73) Assignee: NIPRO CORPORATION, Osaka (JP)

( * ) Notice: Subject to any disclaimer, the term of this patent is extended or adjusted under 35 U.S.C. 154(b) by 337 days.

(21) Appl. No.: 15/544,946

(22) PCT Filed: Feb. 19, 2016

(86) PCT No.: PCT/JP2016/054830
§ 371 (c)(1),
(2) Date: Jul. 20, 2017

(87) PCT Pub. No.: WO2016/136609
PCT Pub. Date: Sep. 1, 2016

(65) Prior Publication Data
US 2018/0015260 A1  Jan. 18, 2018

(30) Foreign Application Priority Data

Feb. 27, 2015 (JP) .............................. JP2015-037783
May 11, 2015 (JP) .............................. JP2015-096232

(51) Int. Cl.
*A61M 25/09* (2006.01)

(52) U.S. Cl.
CPC ... *A61M 25/09* (2013.01); *A61M 2025/09066* (2013.01); *A61M 2025/09083* (2013.01);
(Continued)

(58) Field of Classification Search
None
See application file for complete search history.

(56) References Cited

U.S. PATENT DOCUMENTS 4,619,274 A * 10/1986 Morrison .............. A61M 25/09
600/434
4,884,579 A * 12/1989 Engelson .............. A61M 25/09
600/585
(Continued)

FOREIGN PATENT DOCUMENTS

EP  2313143 A1  4/2011
JP  07227429 A * 8/1995 ............ A61M 25/09
(Continued)

OTHER PUBLICATIONS

Extended European Search Report for European Patent Application No. 16755355.1 dated Sep. 20, 2018, 8 pages.
(Continued)

*Primary Examiner* — Michael R Bloch
(74) *Attorney, Agent, or Firm* — Edell, Shapiro & Finnan, LLC

(57) ABSTRACT

Provided is a guide wire having a novel structure, with which it is possible to improve production efficiency and to effectively prevent large irregularities from forming on an outer circumferential surface of a core wire. Further provided is a guide wire having a novel structure, with which it is possible to more meticulously set bending rigidity to a distal end portion thereof. In a guide wire having a coil externally mounted about a distal end portion of a core wire, a proximal end portion of the coil is integrally joined to the core wire during formation of the coil. Furthermore, in a guide wire having a coil externally mounted about a distal end portion of a core wire, a cross-sectional shape of a wire that constitutes the coil varies in a lengthwise direction of the coil.

13 Claims, 3 Drawing Sheets

(52) U.S. Cl.
CPC ............. *A61M 2025/09108* (2013.01); *A61M 2025/09175* (2013.01); *A61M 2025/09191* (2013.01)

(56) References Cited

U.S. PATENT DOCUMENTS

| | | | |
|---|---|---|---|
| 5,636,641 A * | 6/1997 | Fariabi | A61F 2/958 600/37 |
| 6,348,041 B1 * | 2/2002 | Klint | A61M 25/09 600/585 |
| 2004/0059258 A1 | 3/2004 | Campion et al. | |
| 2005/0148901 A1 | 7/2005 | Parins et al. | |

FOREIGN PATENT DOCUMENTS

| | | |
|---|---|---|
| JP | H7-227429 A | 8/1995 |
| JP | 2001-238962 A | 9/2001 |
| JP | 2001-340467 A | 12/2001 |
| JP | 2002-539901 A | 11/2002 |
| JP | 2007-503256 A | 2/2007 |
| JP | 2012-210292 A | 11/2012 |
| WO | 0057944 A1 | 10/2000 |

OTHER PUBLICATIONS

International Search Report for PCT/JP2016/054830 dated Mar. 22, 2016.
English Translation of International Preliminary Report for PCT/JP2016/054830, dated Sep. 8, 2017.
First Office Action in related Japanese Patent Application No. 2017-502318, dated Nov. 5, 2019, 10 pages (including English translation).
First Office Action in related Chinese Patent Application No. 201680007778.2, dated Oct. 9, 2019, 16 pages (including English translation).
Notice of Reasons for Refusal received in Japanese patent application No. 2017-502318, dated May 15, 2020 (9 pages).
European Office Action received in corresponding European Patent Application No. 16755355.1, dated Apr. 20, 2020 (5 pages).
Chinese Office Action received in corresponding Chinese Patent Application No. 201680007778.2, dated Apr. 15, 2020 (12 pages).

* cited by examiner

GUIDE WIRE

CROSS REFERENCE TO RELATED APPLICATIONS

This application is 371 National Stage of International Application No. PCT/JP2016/054830, filed on Feb. 19, 2016, and claims priority under 35 U.S.C. § 119 to Application No. JP2015-037783 filed on Feb. 27, 2015, and Application No. JP2015-096232 filed on May 11, 2015, the entire contents of which are hereby incorporated by reference.

TECHNICAL FIELD

The present invention relates to a guide wire for guiding a medical tube such as a catheter or the like to a prescribed position of a somatic lumen such as a blood vessel or the like.

BACKGROUND ART

Conventionally, in the medical field, medical tubes such as various types of catheters or the like have been used. For example, by inserting a catheter into a somatic lumen such as a blood vessel or the like, liquid medicine or the like can be injected, or biological fluid can be collected. In addition, treatments, inspections or the like can be performed with a device inserted into a body through that catheter. Also, with medical instruments such as a dialyzer or the like as well, catheters are used when providing passages for blood or liquid medicine outside the body.

Here, guide wires are typically used in order to insert such catheters to a prescribed position of the somatic lumen. Specifically, before insertion of a catheter, a guide wire is inserted in advance into the desired somatic lumen, and then, the catheter is slipped externally about the guide wire, for example. By inserting the catheter into the body in this state, the catheter is guided by the guide wire and configured to be introduced to the prescribed position of the somatic lumen. Such guide wires are cited in, for example, Japanese Unexamined Patent Publication No. JP-A-2012-210292 (Patent Document 1) or Japanese Domestic Publication of International Patent Application No. JP-A-2007-503256 (Patent Document 2), which disclose a structure including an elongated core wire and a coil externally mounted about the distal end portion of the core wire.

Meanwhile, with the guide wire described in Patent Document 1, the core wire and the coil are formed as separate parts. After placing the coil externally about the distal end portion of the core wire, the prescribed positions of these parts are brazed and secured to each other, thereby producing the guide wire.

However, since the operation is required for inserting the core wire into the coil and then securing the two parts, there is a risk that production may be very troublesome. Besides, irregularities will greatly occur between these two parts due to brazing, posing a problem that the devices such as a catheter may be caught by the irregularities and find it difficult to proceed, or the like.

Also, for the guide wire, in general, it is preferable that the proximal end side thereof has sufficient pushability in order to be inserted into the lumen, while the distal end side thereof has sufficient flexibility in order to deform by following the bending or curving lumen. With the guide wire described in Patent Document 2, since the coil is externally mounted about its distal end portion, owing to the coil, the guide wire is able to flexibly deform in a direction orthogonal to the lengthwise direction as well. In particular, with the guide wire described in Patent Document 2, the portion of the core wire to which the coil is mounted becomes smaller in diameter toward its distal end, so that the guide wire is configured to deform more flexibly toward its distal end.

However, with the guide wire described in Patent Document 2, flexibility, namely change in bending rigidity, of the distal end portion is adjusted only by the diameter dimension of the core wire. This makes it difficult to meticulously set the bending rigidity to the distal end portion of the guide wire.

BACKGROUND ART DOCUMENTS

Patent Documents

Patent Document 1: JP-A-2012-210292
Patent Document 2: JP-A-2007-503256

SUMMARY OF THE INVENTION

Problem the Invention Attempts to Solve

The present invention has been developed in view of the above-described matters as the background, and it is an object of the present invention to provide a guide wire with a novel structure which is able to improve production efficiency while effectively preventing occurrence of large irregularities on the outer circumferential surface of the core wire.

Moreover, it is another object of the present invention to provide a guide wire with a novel structure which makes it possible to more meticulously set the bending rigidity to the distal end portion thereof.

Means for Solving the Problem

A first mode of the present invention provides a guide wire including a core wire and a coil externally mounted about a distal end portion of the core wire, characterized in that: a proximal end portion of the coil is integrally joined to the core wire during formation of the coil.

With the guide wire constructed according to the present mode, the coil is formed in the state of being integrally joined to the core wire. This makes it possible to omit the operation of producing the coil separately from the core wire and placing the coil externally about the core wire. By so doing, production efficiency of the guide wire can be improved. Moreover, for example, since the process of brazing and joining the coil to the core wire or the like is not necessary, at least occurrence of depressions or ridges on the outer circumferential surface of the core wire due to brazing will be effectively prevented, and even if the depressions or ridges occur, they can be kept to a minimum. Accordingly, the guide wire can be effectively prevented from being caught by the lumen wall or the like when being inserted into the lumen.

A second mode of the present invention provides a guide wire including a core wire and a coil externally mounted about a distal end portion of the core wire, characterized in that: a cross-sectional shape of a wire that constitutes the coil varies in a lengthwise direction of the coil.

With the guide wire constructed according to the present mode, by having the cross-sectional shape of the coil wire varied in the lengthwise direction, it is possible to vary the bending rigidity of the coil, and to appropriately set the bending rigidity of the distal end portion of the guide wire in accordance therewith. In particular, the coil positioned so as to be remote radially outward from the central axis of bending of the guide wire undergoes a large deformation during bending deformation of the guide wire. Thus, the variation of the cross-sectional shape of the coil wire will be effectively reflected on the bending rigidity of the distal end portion of the guide wire. Therefore, by varying the cross-sectional shape of the coil wire in the lengthwise direction, the bending rigidity of the distal end portion of the guide wire can be set effectively as well as meticulously.

It should be appreciated that in the present invention, the mode wherein the cross-sectional shape of the coil wire varies is not limited to the mode wherein the shape of the cross section of the coil wire varies but includes the mode wherein the shape of the cross section is similar and only the size thereof varies.

A third mode of the present invention provides the guide wire according to the first or second mode, wherein the distal end portion of the core wire about which the coil is externally mounted has a tapered shape.

With the guide wire constructed according to the present mode, since the outside diameter dimension, namely the cross-sectional shape, of the core wire varies in the lengthwise direction, the bending rigidity of the core wire itself varies in the lengthwise direction as well. By so doing, the bending rigidity of the distal end portion of the guide wire can be set with a higher degree of freedom in consideration of the cross-sectional shapes of both the core wire and the coil. Specifically, it is possible to separately set each cross-sectional shape of the coil wire and the core wire, thereby setting the bending rigidity of the guide wire more meticulously.

In particular, since the distal end portion of the core wire has a tapered shape, the bending rigidity of the distal end side can be set low so as to be flexibly deformable, while the bending rigidity of the proximal end side can be set high so as to provide excellent pushability. Such a mode can also be easily realized.

A fourth mode of the present invention provides the guide wire according to any of the first through third modes, wherein a cross-sectional area of a wire that constitutes the coil is made smaller on a distal end side rather than on a proximal end side of the coil.

With the guide wire constructed according to the present mode, it is possible to set a low bending rigidity to the distal end side of the coil, while the proximal end side of the coil can obtain a high bending rigidity. In particular, in combination with the second mode, each cross-sectional area of the coil wire and the core wire can be made smaller on the distal end side rather than on the proximal end side, thereby making the distal end portion of the guide wire even more flexibly deformable.

A fifth mode of the present invention provides the guide wire according to any of the first through fourth modes, wherein at least a portion of the coil in a lengthwise direction is formed with a wire whose cross-sectional shape has a larger width dimension on a radially outer end rather than on a radially inner end thereof.

With the guide wire constructed according to the present mode, the cross section of the coil wire is made larger on the radially outer side rather than on the radially inner side. By so doing, on the radially inner side, the cross section of the coil wire is made small in area, so as to be readily deformable, while on the radially outer side, the gaps between the coil wires are made small, so as to reduce contact resistance with respect to the inner surface of the lumen or the like.

Besides, on the radially inner side of the coil, it would also be acceptable to design such that the gaps between the adjacent coil wires are made large so as to avoid contact interference during bending deformation of the coil, thereby allowing the coil to bend even more easily.

Note that as the cross-sectional shape of the coil wire in the present mode, preferably adopted are, for example, a triangle whose base is defined by the radially outer side of the coil and whose vertex is on the radially inner side of the coil, a trapezoid whose lower base is defined by the radially outer side of the coil and whose upper base is on the radially inner side of the coil, or the like.

A sixth mode of the present invention provides the guide wire according to any of the first through fifth modes, wherein an outside diameter dimension of the coil is approximately constant across an entire length thereof.

The guide wire constructed according to the present mode is able to reduce the risk that the coil is caught by the lumen wall when the guide wire is inserted into the lumen, thereby attaining smooth insertion of the guide wire. The present mode will be advantageously realized by making the winding diameter (outside diameter) of the coil approximately constant across the entire length of the coil. Particularly in the present mode, it is desirable that, in the state where the central axis of the core wire is in a linear pattern without deformation, there be almost no gaps between the adjacent wires of the coil which is placed externally about the core wire. By so doing, depressions or ridges between the wires that are adjacent in the lengthwise direction of the coil can be made small.

A seventh mode of the present invention provides the guide wire according to any of the first through fifth modes, wherein an outside diameter dimension of the coil is made smaller on a distal end side rather than on a proximal end side thereof.

With the guide wire constructed according to the present mode, it will be easy to set such that the bending rigidity of the coil is lower on the distal end side rather than on the proximal end side thereof. This makes it possible for the distal end portion of the guide wire to have even greater flexibility, so as to be able to easily deform in conformity with the bending portion of the lumen.

An eighth mode of the present invention provides the guide wire according to any of the first through seventh modes, wherein the core wire includes a mounting part to which the coil is mounted and a stepped part provided on a proximal end side of the mounting part, and the mounting part positioned on a distal end side beyond the stepped part is reduced in diameter.

With the guide wire constructed according to the present mode, the coil is mounted to the mounting part which is positioned on the distal end side beyond the stepped part and is reduced in diameter. By so doing, it is possible to minimize the differential between the wire outside diameter of the non-mounting part of the core wire to which no coil is mounted and the coil outside diameter of the coil mounting part that are positioned on the opposite sides of the stepped part, namely the substantial projecting dimension of the coil from the outer circumferential surface of the core wire. This will decrease the risk of the coil being caught by the lumen wall when inserting and removing the guide wire with respect to the lumen. Note that it is preferable that the differential between the outside diameter dimensions of the mounting part and the non-mounting part of the core wire that are positioned on the opposite sides of the stepped part, namely the step height of the stepped part, is made approximately equal to the diameter dimension of the coil wire.

With this arrangement, the substantial projecting dimension of the coil from the outer circumferential surface of the core wire will be sufficiently minimized, so that the coil mounting part and the non-mounting part of the guide wire are connected even more smoothly on the outer circumferential surfaces thereof.

A ninth mode of the present invention provides the guide wire according to any of the first through eighth modes, wherein a material of a wire that constitutes the coil varies in a lengthwise direction of the coil.

With the guide wire constructed according to the present mode, by varying the material of the coil wire, deformation characteristics can be designed with even higher degree of freedom. For example, the coil wire made of a material such as stainless steel or the like can be partially made of a material such as platinum or the like that exhibits radiopaqueness. By so doing, a coil which is recognizable under the X-ray fluoroscopy can also be obtained. Note that the coil according to the present mode may be obtained by connecting the coils formed of different materials in advance through welding or the like, or may be obtained by, for example, joining the wire formed by electroforming to the wire formed of a different material at the same time of the formation. Also, in the case of being combined with the second mode, no correlation is required between the location at which the cross-sectional shape changes and the location at which the material changes in the lengthwise direction of the wire that constitutes the coil.

A tenth mode of the present invention provides the guide wire according to any of the first through ninth modes, wherein a wire that constitutes the coil is formed by at least one of electroforming and etching.

With the guide wire constructed according to the present mode, the coil whose cross-sectional shape or material varies in the lengthwise direction can be obtained. In comparison with the case where the coil is formed by cutting or the like, by adopting electroforming or the like, the portion to be discarded will be reduced, thereby achieving a higher yield. Note that in order to obtain the coil for which the cross-sectional shape of the wound wire varies in the lengthwise direction, it would be possible to form a wire whose cross-sectional shape varies in the lengthwise direction by at least one of electroforming and etching, then wind the wire so as to form the coil. Alternatively, it would also be acceptable to directly form the coil having a shape for which a wire whose cross-sectional shape varies in the lengthwise direction is wound with a prescribed winding diameter, by at least one of electroforming and etching.

In addition, with the guide wire of the present mode, it is not necessary for the coil wire to be formed by electroforming or etching across the entire length thereof. For example, it would also be possible to adopt a structure in which a partial coil is obtained by winding a wire formed by drawing process or the like, then a coil comprising a wire formed by electroforming or etching is connected to that partial coil.

An eleventh mode of the present invention provides the guide wire according to any of the first through ninth modes, wherein a wire that constitutes the coil is formed by at least one of thermal spraying and vacuum deposition.

With the guide wire constructed according to the present mode as well, the same as with the tenth mode, the portion to be discarded will be reduced in comparison with the case where the coil is formed by cutting or the like, whereby a higher yield can be achieved. In particular, with the present mode, the guide wire is formed by thermal spraying or vacuum deposition. This will increase a degree of freedom in choosing the material of the guide wire, so that the guide wire can also be formed with a material having a lower bending rigidity. By so doing, change in bending rigidity in the lengthwise direction of the guide wire can be made greater, thereby making it possible to more meticulously set the bending rigidity. Besides, a degree of freedom in setting the shape of the coil will be higher than in the case where the coil is formed by cutting or the like, so that manufacture of a coil having a complicated shape will be possible with a high dimensional accuracy in an efficient and practical manner.

Effect of the Invention

With the guide wire constructed according to the first mode, since the core wire and the coil are integrally formed, production efficiency can be improved. Moreover, occurrence of irregularities due to brazing will be limited, so that depressions or ridges at the connected section of the core wire and the coil can be minimized.

Also, with the guide wire constructed according to the second mode, the cross-sectional shape of the coil externally mounted about the distal end portion thereof varies in the lengthwise direction. This makes it possible to meticulously set the bending rigidity of the distal end portion of the guide wire.

BRIEF DESCRIPTION OF THE DRAWINGS

FIGS. 4A-4C are enlarged views of principal parts of FIG. 3, wherein FIG. 4A shows a proximal end portion of a coil, FIG. 4B shows a lengthwise medial portion of the coil, and FIG. 4C shows a distal end portion of the coil.

EMBODIMENTS FOR CARRYING OUT THE INVENTION

Embodiments of the present invention will be described below in reference to the drawings.

Figure 1:
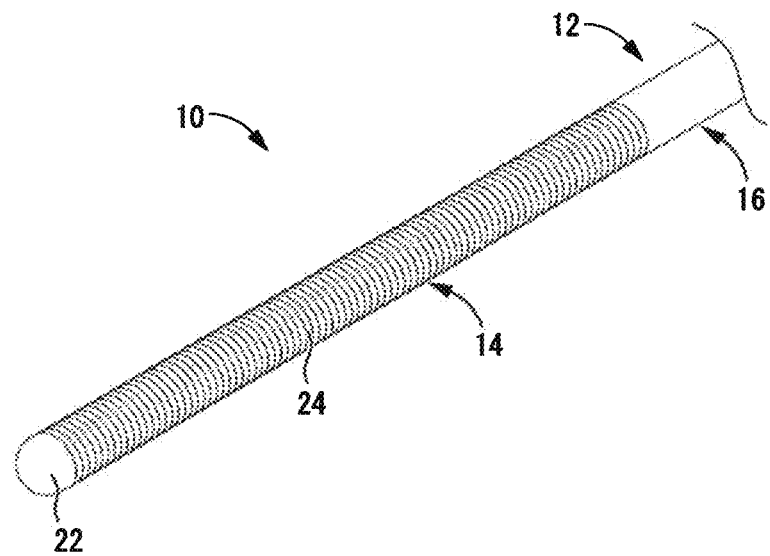
FIG. 1 is a perspective view showing a guide wire as a first embodiment of the present invention.
Figure 2:
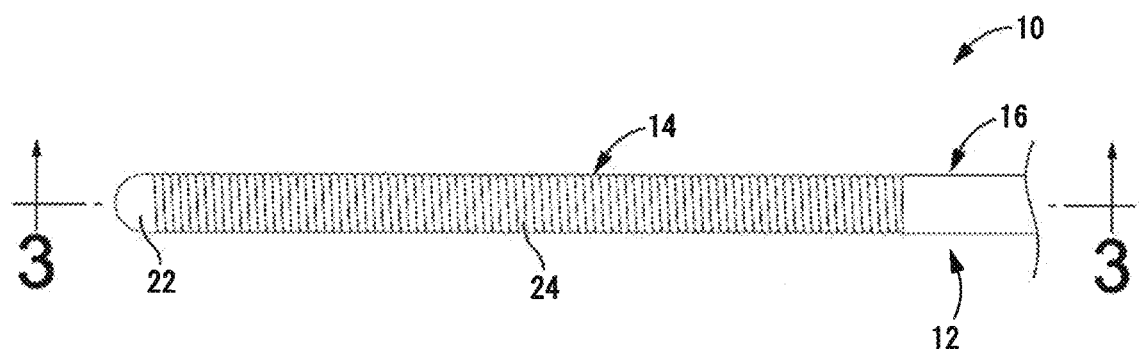
FIG. 2 is a front view of the guide wire shown in FIG. 1.
Figure 3:
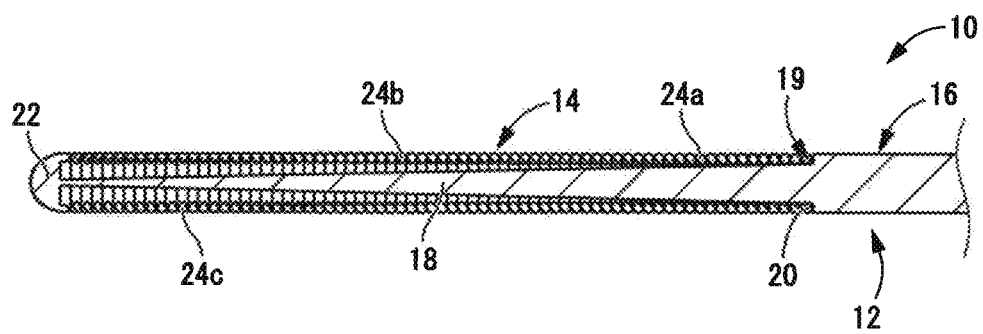
FIG. 3 is a cross sectional view taken along line 3-3 of FIG. 2.

First, FIGS. 1 through 3 depict a guide wire 10 as a first embodiment of the present invention. The guide wire 10 includes a core wire 12 extending in an elongated shape and a coil 14 externally mounted about a distal end portion of the core wire 12. Prior to insertion of a catheter or the like into a lumen, the guide wire 10 is configured to be inserted into that lumen so as to guide the catheter or the like to a prescribed position in the lumen during its insertion. In the description hereinbelow, the axial direction refers to the lateral direction in FIG. 2, in which the guide wire 10 extends. Also, the distal end side refers to the left side in FIG. 2, which is the side configured to be inserted into the lumen of the patient. Meanwhile, the proximal end side refers to the right side in FIG. 2, which is the side to be operated by a user of the guide wire 10.

Described more specifically, the core wire 12 is a small-diameter wire that extends in the axial direction overall, and includes a main body part 16 and a mounting part 18 positioned on the distal end side of the main body part 16. These main body part 16 and mounting part 18 are integrally formed, and the main body part 16 continuously extends in the axial direction with a generally constant outside diameter dimension. Note that the proximal end portion of the main body part 16 may be provided with an operating part having a large outside diameter dimension or the like so that the user readily grips and operates the core wire 12, namely the guide wire 10. Moreover, the surface of the main body part 16 and the coil 14 may be coated with a synthetic resin such as PTFE or the like.

Regarding the mounting part 18, the diametrical dimension varies in the axial direction, and has a tapered shape whose outside diameter dimension gradually decreases toward its distal end side. Whereas the mounting part 18 preferably has a shape whose diameter decreases toward its distal end side, no limitation is imposed thereon. For example, the mounting part 18 may extend in the axial direction with a generally constant outside diameter dimension, or may alternatively decreases its diameter in a stepwise manner toward its distal end side.

In the present embodiment, the outside diameter dimension of the proximal end portion of the mounting part 18 is made smaller than the outside diameter dimension of the main body part 16, so that a stepped part 19 is formed at the connected section of the main body part 16 and the mounting part 18, with an annular stepped face 20 provided so as to extend in the axis-perpendicular direction.

Besides, to the distal end of the mounting part 18, a distal end tip 22 is secured by welding, bonding, or the like. The distal end tip 22 has a solid, approximately semispherical shape overall, and is attached so as to be convex to the distal end side.

Such a core wire 12 is preferably formed of a metal having elasticity, for example, a stainless steel. The main body part 16 and the mounting part 18 can be integrally formed, for example, preferably by using an elongated wire made of stainless steel and cutting its distal end portion so as to form the mounting part 18. Alternatively, the main body part 16 and the mounting part 18 may be integrally formed by electroforming, or may be provided by the mounting part 18 formed by cutting or electroforming being secured to the distal end of the main body part 16 constituted by a wire.

Then, the coil 14 is externally mounted about the mounting part 18 of the core wire 12. The coil 14 has a structure in which a coil wire 24 serving as a wire made of a single, small-diameter wire or the like is wound in a spiral shape. By the cross-sectional shape of the coil wire 24 being varied in the lengthwise direction, the cross-sectional shape of the coil 14 varies in the lengthwise direction as well. Note that the lengthwise dimension (the lateral dimension in FIG. 2) of the coil 14 is made approximately equal to the length dimension of the mounting part 18 of the core wire 12.

Figure 4A:
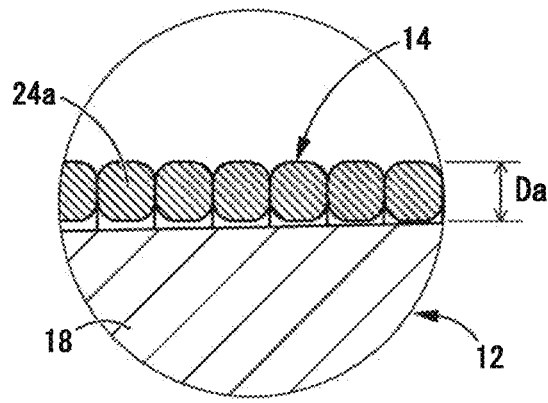
Figure 4B:
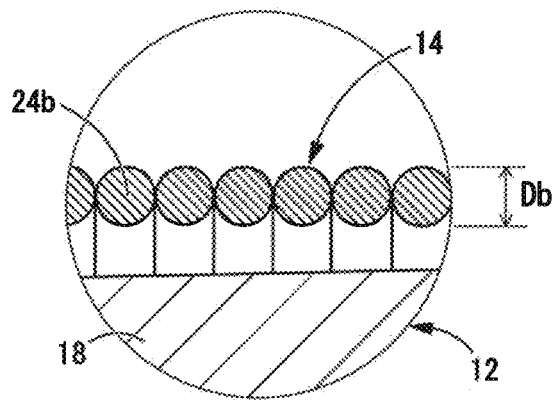
Figure 4C:
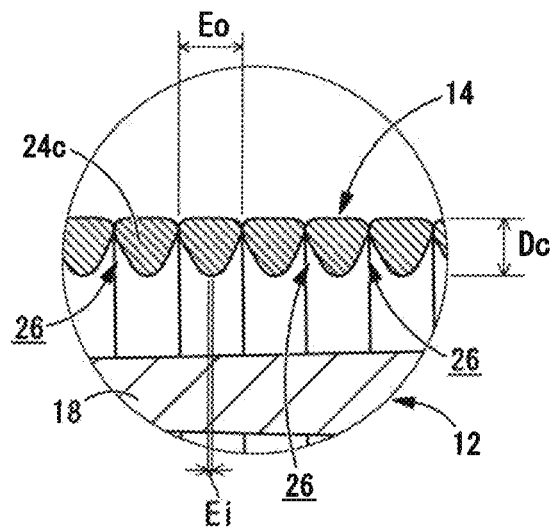

In the present embodiment, as shown in FIGS. 4A through 4C, the cross-sectional shape of a coil wire 24a at the proximal end portion of the coil 14 is an approximately rectangular shape, and in this embodiment in particular, the cross-sectional shape of the coil wire 24a is a square. Besides, the cross-sectional shape of a coil wire 24b at the lengthwise medial portion of the coil 14 is a circular shape (or may be an elliptical shape). Moreover, the cross-sectional shape of a coil wire 24c at the distal end portion of the coil 14 is an approximately triangular shape, and in this embodiment in particular, the cross-sectional shape of the coil wire 24c is an approximately equilateral triangle. With this arrangement, the cross-sectional area of the coil wire 24 that constitutes the coil 14 becomes smaller in a stepwise manner from its proximal end side toward its distal end side. Note that in the present embodiment, the height dimension Da of the square, namely the cross-sectional shape of the coil wire 24a at the proximal end portion of the coil 14 (see FIG. 4A), the diameter dimension Db of the circle, namely the cross-sectional shape of the coil wire 24b at the lengthwise medial portion of the coil 14 (see FIG. 4B), and the height dimension Dc of the equilateral triangle, namely the cross-sectional shape of the coil wire 24c at the distal end portion of the coil 14 (see FIG. 4C) are made approximately equal (Da=Db=Dc). Furthermore, in the present embodiment, the corner of each cross section of the coil wires 24a, 24c at the proximal end portion and the distal end portion of the coil 14 respectively has a chamfer-like round surface, so that each corner of the square and the equilateral triangle, which are their respective cross-sectional shapes, is rounded.

It should be appreciated that at the distal end portion of the coil 14, the base of the triangle, which is the cross-sectional shape of the coil wire 24c, is positioned on the outer circumferential surface of the coil 14, and its vertex is positioned on the radially inner end of the coil 14. In other words, when viewed in vertical cross section of the distal end portion of the coil 14, with respect to the coil wire 24c, the dimension Eo in the lengthwise direction of the coil on its radially outer end (see FIG. 4C) and the dimension Ei in the lengthwise direction of the coil on its radially inner end (see FIG. 4C) are made different. In the present embodiment, the lengthwise dimension Ei of the radially inner end is made substantially minimal (0). Thus, the lengthwise dimension Eo of the radially outer end is made larger than the lengthwise dimension Ei of the radially inner end. With this arrangement, on the radially outer side of the coil 14, the wires are in contact or close to each other in the lengthwise direction, while on the radially inner side of the coil 14, there are formed relatively large gaps 26 between the wires adjacent to each other in the lengthwise direction so as to expand radially inward.

Such a coil 14 can be formed by a publicly-known coil manufacturing method wherein, for example, the coil wire 24 to which the cross-sectional shape that varies in the lengthwise direction is given as described above is wound around a core rod in a spiral shape, then the core rod is removed, and after-processing such as hardening or the like is performed as needed. Note that in the present embodiment, the outside diameter dimension (the winding diameter) of the coil 14 is approximately constant across roughly the entire length in the lengthwise direction.

Also, such a coil wire 24 is made of metal such as stainless steel or the like for example, and can be formed by cutting a stainless steel wire or by electroforming. Note that whereas the coil wire 24 may be formed by using a single wire, it would also be acceptable that the proximal end portion 24a whose cross section is an approximate square, the medial portion 24b whose cross section is a circle, and the distal end portion 24c whose cross section is an approximately equilateral triangle are connected to one another by welding or the like before or after being wound or the like to form the coil.

Moreover, the material of the coil wire 24 may vary in the lengthwise direction. As a specific example, the portion of the distal end or the like of the coil wire 24 may be made of a material such as platinum or the like that exhibits radiopaqueness across a prescribed length thereof. At that time, the portion of the coil wire 24 made of platinum and the portion made of stainless steel may be connected by welding or the like, or may alternatively be formed integrally by electroforming. In this way, by varying the material of the coil 14 in the lengthwise direction so as to integrally form a portion which is visible under the X-ray fluoroscopy for example, it is possible to omit a labor of mounting a marker such as platinum or the like after forming the coil. It should be appreciated that in the case where the material of the coil wire varies in the lengthwise direction, no correlation is required between the location at which the cross-sectional shape changes in the coil wire and the location at which the material changes in the coil wire.

By the coil 14 having the above-described shape being placed externally about the mounting part 18 of the core wire 12, and the distal end tip 22 being attached to the distal end of the mounting part 18 by securing or the like, the guide wire 10 of the present embodiment is constituted. At that time, it is preferable that at the stepped face 20 of the core wire 12 or at the proximal end portion of the mounting part 18, the core wire 12 and the proximal end of the coil 14 are secured by welding, bonding or the like, while the proximal end of the distal end tip 22 and the distal end of the coil 14 are secured by welding, bonding or the like.

Note that in the present embodiment, the dimension of the stepped face 20 in the height direction (the vertical direction in FIG. 3) and the height dimension Da of the coil wire 24a at the proximal end portion of the coil 14 are made approximately equal. By so doing, the outside diameter of the main body part 16 positioned on the lengthwise proximal end side of the wire beyond the stepped part 19 and the outside diameter (the winding diameter) of the coil 14 are made approximately equal, so that their outer circumferential surfaces are connected from the main body part 16 to the coil 14 with almost no irregularities. Besides, regarding the coil 14 as well, the coil winding diameter (the coil outside diameter) is made approximately constant across the entire length in the lengthwise direction from the proximal end portion, going through the medial portion, and further up to the distal end portion.

With the guide wire 10 of the present embodiment having the above-described shape, when the distal end portion of the guide wire 10 undergoes curving deformation, the coil 14 also undergoes bending deformation together with the distal end portion of the core wire 12. In particular, the coil 14 flexibly conforms to the curving deformation of the guide wire 10, while being capable of having a sufficient influence on curving deformation characteristics of the guide wire 10. Also, as is well known, the deformation of the coil 14 arises accompanied mainly by torsional deformation of the coil wire 24. Thus, by adjusting the cross-sectional shape of the coil wire 24 or the like and appropriately setting the polar moment of inertia of area or the like, it is possible to design elastic deformation characteristics of the coil 14. Therefore, variation in the cross-sectional shape of the coil wire 24 in the lengthwise direction as in the present embodiment makes it possible to meticulously adjust bending deformation characteristics of the distal end portion of the coil 14 and hence the guide wire 10, and to tune them to the required characteristics. Besides, in this embodiment in particular, the mounting part 18 of the core wire 12 is tapered and the moment of inertia of area is varied in the axial direction, so that the bending rigidity of the core wire 12 also becomes lower toward the distal end side. Accordingly, the bending rigidity at the distal end portion of the guide wire 10 can be adjusted and set even more meticulously by combining both the core wire 12 and the coil 14.

In this embodiment in particular, since the mounting part 18 has a tapered shape, the moment of inertia of area changes in the lengthwise direction, and since the cross-sectional area of the coil wire 24 is made smaller on the distal end side rather than on the proximal end side, the polar moment of inertia of area changes in the lengthwise direction. Owing to additive action of these matters, with the guide wire 10, the bending rigidity on the distal end side is made sufficiently smaller than that on the proximal end side. This allows the distal end of the guide wire 10 to readily deform by following the bending lumen, while concomitantly being capable of providing excellent pushability to the guide wire 10.

Also, in the present embodiment, the cross section of the coil wire 24c at the distal end portion of the coil 14 is an approximate triangle whose vertex is on the radially inner side of the coil 14. Accordingly, between the adjacent coil wires 24c, the gaps 26 are set so as to have the cross-sectional shape that gradually expands radially inward. Therefore, on the outer circumferential surface of the coil 14, the base of the coil wire 24c is positioned, and depressions or ridges, or gaps are made small on the outer circumferential surface of the coil 14, so as to minimize contact resistance with respect to the inner surface of the lumen or the like. Meanwhile, on the inner circumferential surface of the coil 14, during curving deformation of the coil 14, interference between the adjacent coil wires 24c can be reduced owing to the gaps 26 set therebetween.

Moreover, in the present embodiment, the winding diameter of the coil wire 24 of the coil 14 (the coil outside diameter) is approximately constant across the entire length thereof in the lengthwise direction. Besides, the outside diameter of the core wire 12 positioned on the proximal end side beyond the stepped face 20 is made approximately equal to the coil outside diameter. Thus, the guide wire 10 can be more effectively prevented from being caught inside the lumen such as the blood vessel or the like.

An embodiment of the present invention has been described in detail above, but the present invention is not limited to those specific descriptions. The present invention may be embodied with various changes, modifications and improvements which may occur to those skilled in the art, and such embodiments are all within a range of the present invention as long as they do not deviate from the intention thereof.

For example, in the preceding embodiment, the cross-sectional shape of the coil wire 24a at the proximal end portion of the coil 14 is an approximate square, the cross-sectional shape of the coil wire 24b at the medial portion of the coil 14 is a circle, and the cross-sectional shape of the coil wire 24c at the distal end portion of the coil 14 is an approximately equilateral triangle. However, the present invention is not limited to such cross-sectional shapes. Specifically, the cross-sectional shape of the coil wire is not limited in any way, but would be acceptable as long as it varies in at least a portion of the lengthwise direction of the coil by being changed stepwise or continuously in the lengthwise direction of the coil. Note that in the present invention, the description that the cross-sectional shape of the coil wire varies includes the cross-sectional shapes whose contours are similar but whose sizes are varied. Therefore, it would also be possible to adopt the mode wherein the cross-sectional shape of the coil has a circular cross section from the proximal end side toward the distal end side across the entire length thereof, while the outside diameter dimension thereof gradually decreases continuously or stepwise, or the like.

Figure 5A:
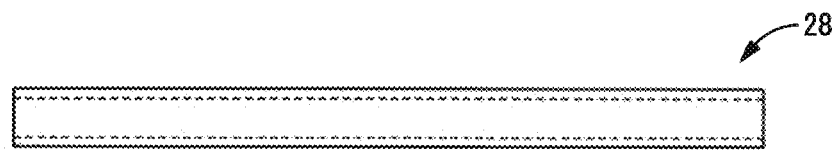
FIGS. 5A-5D are views suitable for explaining a specific example of a method of producing the guide wire according to the present invention.
Figure 5B:
Figure 5C:

Additionally, in the preceding embodiment, after the coil wire 24 is formed, the coil wire 24 is wound around the core rod in a spiral shape so as to form the coil 14. However, the present invention is not limited to such mode. Specifically, as shown in FIGS. 5A through 5D, the coil may be formed by electroforming or etching in the state of being wound in a spiral shape. In specific terms, first, a non-conductive sacrificial material 28 as shown in FIG. 5A is prepared. Then, metal paste is applied on the surface of the sacrificial material 28 in a spiral shape that corresponds to the desired coil shape, and by performing electroforming, as shown in FIG. 5B, the coil having generally constant outside diameter dimension is formed on the outer circumferential surface of the sacrificial material 28. Subsequently, the outer peripheral surface of the coil is subjected to a non-conductive masking so as to be partially covered thereby (the gray portion which is approximately the left half in FIG. 5C), and by performing further electroforming, as shown in FIG. 5C, the coil wire is formed by being thickened through electroforming only on the portion which is not subjected to the masking (the portion which is approximately the right half in FIG. 5C). Then, by immersing the coil in a solvent so as to dissolve the sacrificial material 28 and removing the masking, it is possible to obtain a coil 30 constituted by a coil wire having a cross-sectional shape that varies in the lengthwise direction. Therefore, by placing the coil 30 obtained in this way externally about the mounting part (18) and securing the distal end tip 22 to the distal end of the mounting part (18) as in the preceding embodiment, a guide wire 32 shown in FIG. 5D can be manufactured.

Note that the sacrificial material 28 shown in FIG. 5A has a pipe shape, and whereas the material thereof is not limited in any way as long as it can be dissolved in a solvent, the sacrificial material 28 can be preferably made of, for example, ABS resin, polycarbonate resin, urethane resin, acrylic resin or the like, and moreover, may be molded by a lost-wax process. Also, as the metal paste to be applied on the surface of the sacrificial material 28 in a spiral shape, preferably adopted are, for example, platinum, gold, silver or copper, or mixture paste of them. By so doing, it is possible to manufacture the desired coil 30 using a coil wire made of, for example, platinum, gold, stainless steel, cobalt, chromium, nickel, titanium, or an alloy of them.

Besides, on the outer circumferential surface of the sacrificial material 28 as shown in FIG. 5A, it would also be acceptable that, for example, after a proximal end side coil is electroformed only on the right half, namely the proximal end side thereof, the proximal end side coil is covered by a masking material, and a distal end side coil is electroformed on the left half of the sacrificial material 28. This makes it possible to electroform a coil constituted by a coil wire whose material varies in the lengthwise direction. Also, in the case where the coil is electroformed sequentially and partially in this way, the end of the coil to be electroformed can be joined to the end of the coil wire electroformed earlier simultaneously with the electroforming.

Figure 5D:
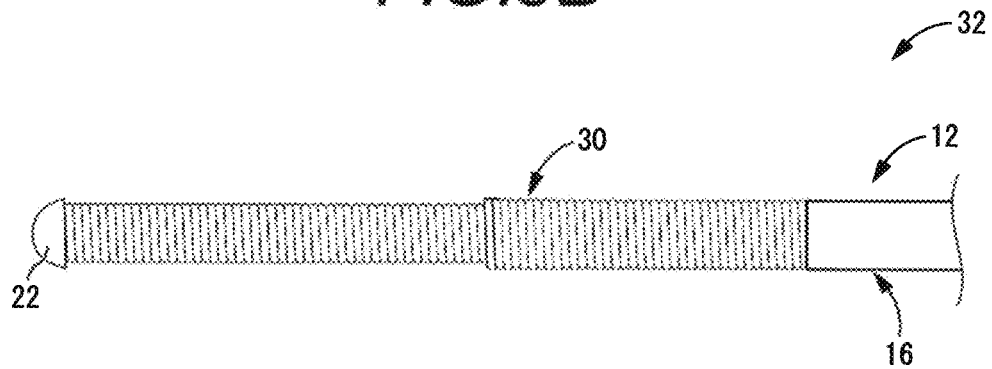

Moreover, with the guide wire 32 shown in FIG. 5D, the proximal end side portion of the coil 30 whose outside diameter dimension is made large and the distal end portion of the main body part 16 of the core wire 12 have outside diameter dimensions which are roughly equal. Note that the outside diameter dimension of the distal end tip 22 may be conformed to the coil diameter of the distal end side portion of the coil 30 whose winding diameter is made small. In addition, with the coil that constitutes the guide wire according to the present invention, as shown in FIG. 5D, the outside diameter dimension may vary in the lengthwise direction. In particular, by the coil being made smaller in diameter on the distal end side rather than on the proximal end side, it is possible to decrease bending rigidity on the distal end side of the guide wire as well as to provide excellent pushability.

Whereas in the manufacturing method of the guide wire 32 shown in FIGS. 5A through 5D, the coil 30 is mounted externally about the mounting part (18) of the core wire 12 after being manufactured by electroforming, the present invention is not limited to such mode. Specifically, it would also be acceptable that the sacrificial material 28 is mounted externally about the mounting part (18) of the core wire 12, and then the electroforming of the coil 30 mentioned above can be performed. This makes it possible to form the wound coil and mount the coil to the core wire 12 simultaneously with the formation of the coil wire.

Furthermore, in the preceding embodiment, the cross-sectional shape of the coil wire 24c at the distal end portion of the coil 14 is an approximate triangle and its vertex angle faces to the radially inner side, so that the gaps 26 expanding toward the radially inner side of the coil 14 are formed between the adjacent coil wires 24c. However, for example, it would also be possible that the vertex angle faces to the radially outer side so that the gaps 26 expanding toward the radially outer side of the coil are formed. Of course, when forming such gaps, it is not necessary for the cross-sectional shape of the coil to be a triangle, but the cross-sectional shape of the coil may be, for example, a trapezoid, a rhombus, a circle, or an ellipse. Specifically, with the cross-sectional shape of the coil wire, as long as the lengthwise dimension is minimal on at least one of the radially inner side and the radially outer side, the gaps can be formed on at least one of the radially inner side and the radially outer side of the coil.

Further, even if the dimension of the stepped face 20 in the height direction and the height dimension Da of the coil wire 24a at the proximal end portion of the coil 14 are not equal, by providing the step between the main body part and the mounting part of the core wire, the outside diameter differential between the core wire and the coil will be minimized, thereby reducing troubles due to such outside diameter differential. However, with the core wire, the outside diameter dimensions of the main body part and the proximal end of the mounting part may be approximately equal, for example. In such case, it can be assumed that a step whose height dimension is approximately 0 is provided between the main body part and the mounting part of the core wire.

Moreover, in the preceding embodiment, the core wire 12 and the coil 14 are separately formed, and then the coil 14 is secured to the core wire 12. However, the coil may be integrally secured to the core wire during formation by electroforming, for example. As a specific example, the surface of the core wire prepared in advance is covered with a non-conductive masking material or a sacrificial material, and only the outer circumferential surface at the proximal end portion of the mounting part which is close to the stepped face is exposed so as to be a joining face. Then, metal paste is applied to the outer circumferential surface of the masking material or the sacrificial material that covers the outer circumferential surface of the mounting part of the core wire in a spiral shape that extends from the joining face to the distal end so as to be an electroforming face. Subsequently, by performing electroforming on the electroforming face so as to electroform the coil and then removing the masking material or the sacrificial material, the coil which is placed externally about the mounting part of the core wire can be obtained. The coil obtained in this way can be secured and joined at its proximal end side end to the joining face of the core wire simultaneously with its formation, thereby obviating special process such as brazing for joining the coil to the core wire or the like. That is, by taking the steps shown in FIGS. 5A through 5C on the outer circumferential surface of the core wire, a coil which is placed externally about the core wire and joined thereto at its proximal end side as shown in FIG. 5D can be obtained simultaneously with its formation. At that time, as described above, the sacrificial material 28 shown in FIG. 5A is configured to be shortened by a prescribed length on the proximal end side, so as to provide the joining face on the outer circumferential surface on the proximal end side of the mounting part of the core wire. Also, in the case where, in the presence of the core wire, the coil is formed on the outer circumferential surface of the mounting part by electroforming or the like and its proximal end portion is integrally secured to the core wire simultaneously with the formation of the coil in this way, even if the stepped face is not provided to the core wire, for example, brazing can be obviated, thereby avoiding projection of the brazed portion to the outer circumferential surface of the core wire. Thus, in comparison with the structure wherein the proximal end portion of the coil is brazed to the core wire, it is possible to minimize the amount of projection of the core wire to the outer circumferential surface.

Note that in the preceding embodiment, it would also be acceptable that, in the presence of the core wire and the coil and with the two components covered with a masking material, a joining part for joining the joining end faces of the two components that are exposed is electroformed by a subsequent process so as to join the core wire and the coil.

In addition, with regard to the distal end tip provided to the distal end of the core wire, in the case where the coil is formed by electroforming or the like, for example, other than attaching later the distal end tip formed separately from the core wire, using a distal end tip integrally formed with the core wire can also be possible. Besides, while FIGS. 5A through 5D described an example of forming the coil 30 by electroforming, in the present invention, it would also be acceptable to adopt etching instead of electroforming, or to adopt electroforming and etching in combination, so as to form the coil or the wire that constitutes the coil.

Furthermore, the coil or the wire that constitutes the coil can also be formed by, instead of electroforming and etching, or in combination with electroforming and etching, adopting thermal spraying or vacuum deposition, which are known as forming technology such as film formation like electroforming. Specifically, for example, the coil or the wire that constitutes the coil may be formed by heating a material to be melted or to be in a state close to being melted, and integrating a multitude of spray particles thereof into a prescribed shape. Also, the coil or the wire that constitutes the coil may be formed by heating a material to be vaporized or to be sublimated, and integrating a multitude of particles thereof into a prescribed shape. By adopting such thermal spraying or vacuum deposition, in comparison with the guide wire formed by electroforming or the like, it is possible to achieve a higher degree of freedom in selecting the material of the guide wire. Therefore, by adopting the material having small rigidity, the bending rigidity of the guide wire can be more decreased, and in association therewith, the amount of change in bending of the guide wire can be increased. This makes it possible to even more meticulously set the bending rigidity in the lengthwise direction of the guide wire.

Note that in the preceding embodiment, the guide wire 10 is made of metal, but by adopting thermal spraying or vacuum deposition, the guide wire can also be made of, for example, synthetic resin or ceramic.

Additionally, each mode of the guide wire described hereinbelow can be recognized as an independent invention capable of solving a different problem from that of the present invention.

A first mode provides a guide wire including a core wire and a coil externally mounted about a distal end portion of the core wire, characterized in that: the core wire includes a mounting part to which the coil is mounted and a stepped part provided on a proximal end side of the mounting part, and the mounting part positioned on a distal end side beyond the stepped part is reduced in diameter.

A second mode provides the guide wire according to the first mode, wherein a proximal end portion of the coil is integrally joined to the core wire during formation of the coil.

A third mode provides the guide wire according to the first or second mode, wherein a cross-sectional shape of a wire that constitutes the coil varies in a lengthwise direction of the coil.

A fourth mode provides the guide wire according to any of the first through third modes, wherein the distal end portion of the core wire about which the coil is externally mounted has a tapered shape.

A fifth mode provides the guide wire according to any of the first through fourth modes, wherein a cross-sectional area of a wire that constitutes the coil is made smaller on a distal end side rather than on a proximal end side of the coil.

A sixth mode provides the guide wire according to any of the first through fifth modes, wherein at least a portion of the coil in a lengthwise direction is formed with a wire whose cross-sectional shape has a larger width dimension on a radially outer end rather than on a radially inner end thereof.

A seventh mode provides the guide wire according to any of the first through sixth modes, wherein an outside diameter dimension of the coil is approximately constant across an entire length thereof.

An eighth mode provides the guide wire according to any of the first through sixth modes, wherein an outside diameter dimension of the coil is made smaller on a distal end side rather than on a proximal end side thereof.

A ninth mode provides the guide wire according to any of the first through eighth modes, wherein a material of a wire that constitutes the coil varies in a lengthwise direction of the coil.

A tenth mode provides the guide wire according to any of the first through ninth modes, wherein a wire that constitutes the coil is formed by at least one of electroforming and etching.

An eleventh mode provides the guide wire according to any of the first through ninth modes, wherein a wire that constitutes the coil is formed by at least one of thermal spraying and vacuum deposition.

KEYS TO SYMBOLS 10, 32: guide wire, 12: core wire, 14, 30: coil, 18: mounting part, 19: stepped part, 24: coil wire

The invention claimed is:
1. A guide wire comprising:
a core wire; and
a coil wire that constitutes a coil externally mounted about a distal end portion of the core wire, wherein
a cross-sectional shape of the coil wire varies in a lengthwise direction of the coil;
a cross-sectional area of the coil wire becomes smaller from a proximal end side of the coil toward a distal end side of the coil; and the cross-sectional shape of the coil wire has a height dimension relative a center axis of the coil that remains the same along the lengthwise direction of the coil.

2. The guide wire according to claim 1, wherein the distal end portion of the core wire about which the coil is externally mounted has a tapered shape.

3. The guide wire according to claim 1, wherein the cross-sectional area of the coil wire is made smaller on a distal end side of the coil than on a proximal end side of the coil.

4. The guide wire according to claim 1, wherein the cross-sectional shape of the coil wire for at least a portion of the coil wire includes inner and outer surfaces relative to a center of the coil, and wherein the outer surface of the cross-sectional shape has a larger width dimension than the inner surface of the cross-sectional shape.

5. The guide wire according to claim 1, wherein an outside diameter dimension of the coil is approximately constant across an entire length thereof.

6. The guide wire according to claim 1, wherein an outside diameter dimension of the coil is smaller on a distal end side thereof than on a proximal end side thereof.

7. The guide wire according to claim 1, wherein the core wire includes a mounting part to which the coil is mounted and a stepped part provided on a proximal end side of the mounting part, and wherein the mounting part positioned on a distal end side of the stepped part is reduced in diameter.

8. The guide wire according to claim 1, wherein a material of the coil wire varies in the lengthwise direction of the coil.

9. The guide wire according to claim 1, wherein the coil wire is formed by at least one of electroforming and etching.

10. The guide wire according to claim 1, wherein the coil wire is formed by at least one of thermal spraying and vacuum deposition.

11. The guide wire according to claim 1, wherein a proximal end portion of the coil is integrally joined to the core wire during formation of the coil.

12. The guide wire according to claim 1, wherein the cross-sectional shape of the coil wire at a distal end portion of the coil is an approximate triangle.

13. The guide wire according to claim 12, wherein the cross-sectional shape of the coil wire at a proximal end portion of the coil is an approximately rectangular shape, while the cross-sectional shape of the coil wire at a medial portion of the coil is a circular shape or an elliptical shape.

* * * * *